United States Patent [19]

Moss et al.

[11] Patent Number: 4,637,678

[45] Date of Patent: Jan. 20, 1987

[54] HOLOGRAPHIC LASER PROTECTION DEVICE

[75] Inventors: Gaylord E. Moss, Marina Del Rey; Mao-Jin Chern, Rancho Palos Verdes; Teena L. Dobbs, Los Angeles, all of Calif.

[73] Assignee: Hughes Aircraft Company, Los Angeles, Calif.

[21] Appl. No.: 384,134

[22] Filed: Jun. 1, 1982

[51] Int. Cl.[4] ............................................. G02B 5/32
[52] U.S. Cl. ......................................... 350/3.7; 350/1.1
[58] Field of Search .................... 350/3.7, 3.73, 3.77, 350/162.17, 162.21, 162.23, 162.2, 3.6, 1.1

[56] References Cited

U.S. PATENT DOCUMENTS

| | | | |
|---|---|---|---|
| 3,675,990 | 7/1972 | Kogelnik et al. | 350/311 |
| 4,245,882 | 1/1981 | Chang | 350/3.77 |
| 4,359,259 | 11/1982 | Horner et al. | 350/3.7 |
| 4,412,719 | 11/1985 | Feinup | 350/3.7 |

FOREIGN PATENT DOCUMENTS 3012550  10/1981  Fed. Rep. of Germany .

OTHER PUBLICATIONS

Johnson et al., "Laser Eye Protection", Final Tech. Report, 8/11/77 to 6/79, FR 79-27-996, Report dated Jul. 1979.

Rao et al., "Holographic Methods for Fabrication of Various Types of Mirrors", pp. 809–813, Rev. Sci. Instrum. 51(6), Jun. 1980.

"Holographic Optics Concentrate Solar Rays", Laser Focus, vol. 17, 12/81—pp. 38, 40.

*Primary Examiner*—Bruce Y. Arnold
*Attorney, Agent, or Firm*—K. W. Float; L. A. Alkov; A. W. Karambelas

[57] ABSTRACT

A holographic reflector for reflecting laser radiation at a predetermined wavelength. The reflector employs a plurality of holograms which are disposed adjacent to one another and which are conterminous with each other. The holograms are generally disposed in a support structure which may be a visor or goggle arrangement. Each of the holograms may be either parallel fringe holograms or slanted fringe holograms. The angular orientation of the fringes and the relative spacing thereof determine the angular coverage provided by the reflector. The reflector provides for reflection of laser radiation at a predetermined wavelength and within a particular angular subtence while allowing high see-through in the visible wavelength region. Multiple sets of holograms may also be stacked in order to protect against multiple laser sources.

12 Claims, 10 Drawing Figures

HOLOGRAPHIC LASER PROTECTION DEVICE

This invention was made with Government support under Contract No. N62269-79-C-D288 awarded by the Department of the Navy. The Government has certain rights in this invention.

BACKGROUND OF THE INVENTION

The present invention relates generally to devices which reflect laser radiation and more particularly to devices which employ holographic elements to reflect the laser radiation.

There are numerous systems employing lasers which are currently utilized by commercial and military users. Such systems include laser communications, ranging, target designation and laser welding systems. Many of these systems employ lasers which emit radiation which can damage the eyes of personnel utilizing the system or being irradiated by the laser radiation of the system. An eye protection device which is designed to protect the eyes from incident radiation is therefore required when utilizing this equipment. Also, thermal imaging systems, and the like, employ detectors which may be damaged if irradiated by laser radiation.

One current method utilized for eye protection involves the use of an absorptive dye along the optical path prior to the eyes. For example, a visor or goggles may incorporate such an absorptive dye in the lens elements in front of the eyes. However, one disadvantage of this method is that the dye absorbs a wide band of wavelengths. This wideband absorption both darkens and tints the image scene that is viewed. The effective visual degradation is generally unacceptable for most applications requiring clear vision.

In another method, conventional multilayer reflection coatings may be applied to a conventional visor in order to reflect the laser radiation. However, these coatings are difficult to apply and it is difficult to obtain adequate protection for both eyes utilizing this method.

Accordingly, it would be an improvement to the laser art to have an eye protection device which adequately protects the eyes from the hazards of incident laser radiation without interfering with normal vision.

It would also be an improvement in the laser art to have a device which can protect the detector elements of electro-optic systems, such as thermal imaging systems, and the like, from damaging laser radiation.

SUMMARY OF THE INVENTION

In order to overcome the problems inherent in prior art eye and detector protection devices, the present invention provides for a holographic reflector which reflects laser radiation at a predetermined wavelength. The device comprises a plurality of conterminous holograms disposed on a substrate or adjacent substrates. This arrangement may be disposed in a support structure. Each of the holograms have holographic fringes which have a predetermined slant angle with respect to a normal to the surface of the substrate. Each of the holograms has a predetermined fringe spacing which is designed to reflect a specific peak wavelength. The combination of holograms of different peak wavelength is designed to reflect the predetermined wavelength over a predetermined angular range. The peak wavelength that each hologram is designed to reflect is generally different from the wavelength which the device is designed to reflect. This utilization of a plurality of holograms to reflect the predetermined wavelength radiation produces a system which is much different than simply utilizing a hologram designed for a given wavelength to reflect that wavelength. The single hologram approach does not have a sufficient angular bandwidth for most applications, whereas the present invention is suitable for wide angular coverage.

In one embodiment, the hologram fringes are parallel to the substrate surface and the fringe spacing of each hologram is selected to reflect the wavelengths required by a composite hologram design. In a predetermined amount. In a second embodiment, the fringes are uniformly slanted with respect to the normal to the substrate surface but are oppositely aligned with respect to each other. The fringe spacing of the two holograms are substantially identical. In a more complex version of this second embodiment, the fringe spacings and slants may be made different in order to achieve an asymmetric angular or wavelength rejection characteristic.

Normally, holographic reflectors reflect in a narrow angular range at a specific wavelength. These reflectors are therefore limited in their ability to protect wide angular areas such as is encompassed by both eyes. However, the present invention provides a reflector to achieve wider angular coverage. This makes it possible to design and construct protective devices with larger angular protection angles with improved transmission at other wavelengths.

Each of the holograms used in the present invention is inherently a narrow-band device. Each single hologram operates by adding the in-phase reflections from a number of recorded layers of varying index of refraction in the hologram material. Only at particular wavelengths and angles does the radiation add in phase to reflect from the hologram. The present invention employs the narrow-band holograms in a manner which provides wide angular coverage suitable for application to eye or sensor protection at the predetermined wavelength. Other wavelengths and angles pass through the holographic reflector unattenuated, providing clear see-through except at the reflection wavelength desired.

Another advantage of utilizing holographic reflection materials is that one recording material may be processed to reflect multiple wavelengths. The hologram may be recorded at a convenient wavelength and then chemically processed to shift it to the desired wavelength. This ability to tailor one recording material to any wavelength is an improvement over the requirement of the dye absorption method to develop different dyes to absorb different wavelengths.

Another advantage of the holographic reflector is its relative independence with respect to shape. The holographic material may be recorded so that its reflecting fringe layers are at an arbitrary angle within the recording medium. This is an improvement over other multilayer devices such as optical coatings in which the layers may only be deposited in parallel to the substrate surface. Accordingly, the multilayer coating approach limits the surface shape of the protection device whereas the holographic reflector device may have an arbitrary shape.

The holographic reflection device of the present invention may also be employed as a reflective element for electro-optic detectors, or the like, in addition to the use with human operators. The holographic reflector may be utilized as an element in front of a detector element or array, or as an aircraft wind screen, or the like.

BRIEF DESCRIPTION OF THE DRAWINGS

The various features and advantages of the present invention may be more readily understood with reference to the following detailed description taken in conjunction with the accompanying drawings, wherein like reference numerals designate like structural elements, and in which:

FIGS. 6 and 7 are graphs illustrating the reflection efficiency with respect to angle of incidence for the holographic reflector embodiments of FIGS. 3a and 4a.

DETAILED DESCRIPTION OF THE INVENTION

Figure 1:
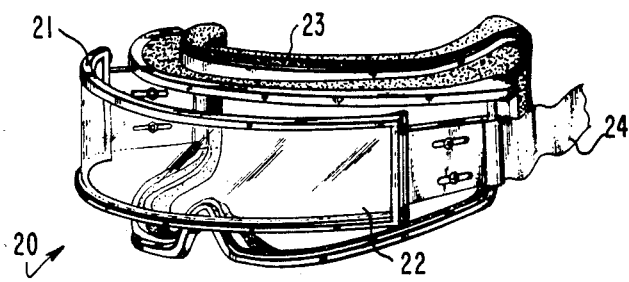
FIG. 1 illustrates a perspective view of an eye protection visor employing the holographic reflector of the present invention.

FIG. 1 shows a perspective view of a holographic reflection visor 20 in accordance with the principles of the present invention. The visor 20 comprises a support structure 21 into which is disposed a holographic reflector 22. The visor 20 includes a face support 23 and a strap 24 for positioning the visor in proper position relative to the eyes of the user.

Figure 2:
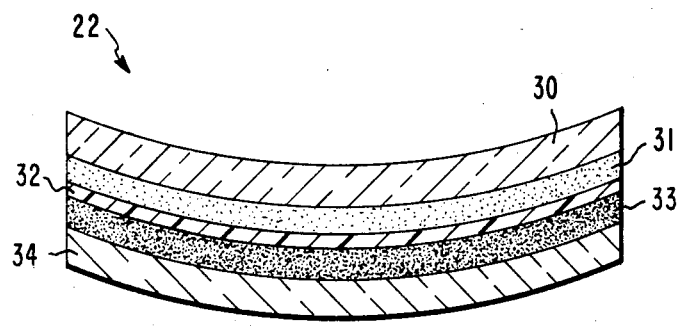
FIG. 2 is a cross-section showing a construction of the holographic reflector of the present invention.

FIG. 2 shows an expanded cross-sectional view of one embodiment of the holographic reflector 22 of the present invention. The reflector 22 is comprised of a first or top substrate 30, which may be comprised of glass or plastic, or the like. A first hologram 31 is disposed on the bottom surface of the first substrate 30. The first hologram may be comprised of a material such as dichromated gelatin, or the like. A second or bottom substrate 34 has a second hologram 33 disposed on the top surface thereof. The two holograms 31, 33 are disposed on their respective substrates 30, 34 so that they may be placed adjacent to each other. The two holograms 31, 33 with their respective substrates 30, 34 are bonded together by means of an adhesive 32, such as transparent epoxy, or the like. The two holograms 31, 33 and their respective substrates 30, 34 are generally conterminous as would be the case when supported in a visor, or the like.

The holographic reflector 22 has a predetermined contour which is determined by the size of the particular visor or goggle arrangement into which the reflector 22 is placed. The holograms 31, 33 have fringes which are formed relative to the particular contour of the respective substrates 30, 34. In a first embodiment, the holographic fringes have a predetermined slant with respect to a normal to the particular substrate. The fringe slant is the angular orientation of the fringes in the hologram with respect to the normal to the surface of the substrate. In the first embodiment, the fringes are parallel to the surface of the substrates 30, 34 of each hologram 31, 33, and the fringe spacing of each hologram 31, 33 differs by a predetermined amount. In a second embodiment the fringes are uniformly slanted with respect to the normal to the surface of the substrates 30, 34 but are oppositely aligned with respect to each other and to the normal. The fringe spacings of the of the two holograms 31, 33 are substantially identical in this embodiment. In a more complex embodiment, the fringe spacings and slant angles may be made different in order to achieve an asymmetric angular or wavelength rejection characteristic.

Figure 2A:
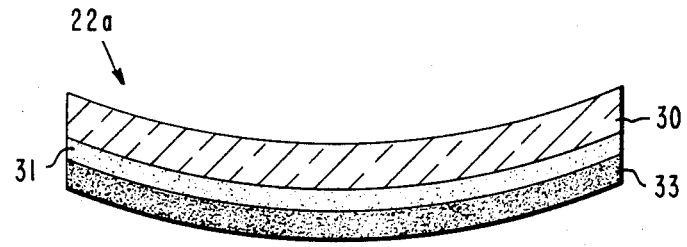
FIG. 2a is a cross-section showing a second construction of the holographic reflector.

FIG. 2a shows a second construction of a holographic reflector 22a. This construction comprises a single substrate 30 onto which both holograms 31, 33 are disposed. Such a construction eliminates the need for a second substrate.

Figure 3A:
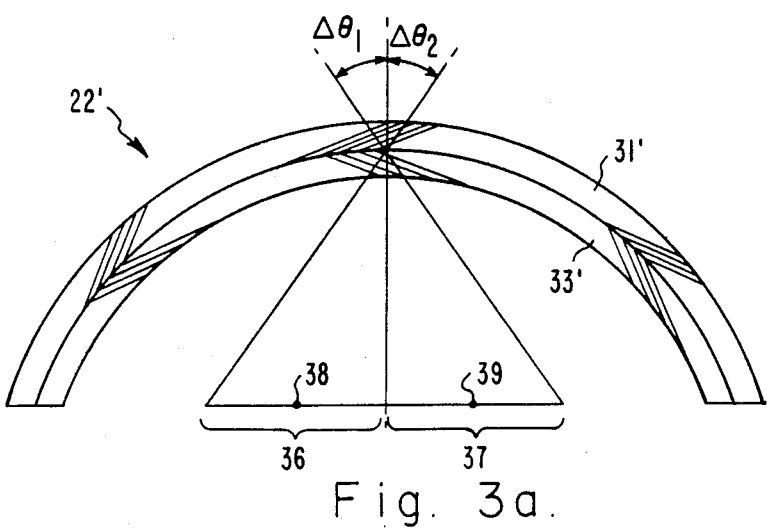
FIGS. 3a and b illustrate visor and goggle designs employing a first embodiment of the holographic reflector of the present invention.
Figure 3B:
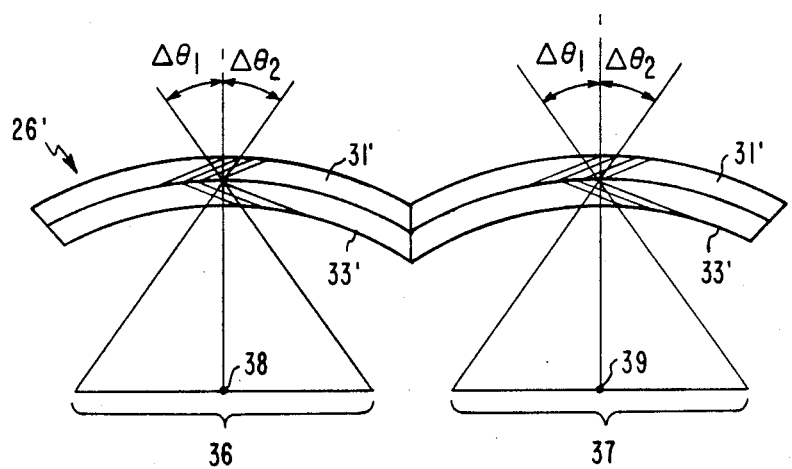

FIG. 3a shows an illustration representative of a portion of a holographic visor employing a holographic reflector 22' in accordance with the present invention. FIG. 3a shows the angular protection provided by a slanted fringe device. As may be seen, each of the holograms 31', 33' reflects laser radiation within a predetermined angular range. As shown, the first hologram 31' reflects within angular range $\Delta\theta_1$, and the second hologram 33' reflects within angular range $\Delta\theta_2$. The fringe angle within each hologram 31', 33' remains the same over the full surface thereof. The angular coverage (shown as brackets 36, 37) provided by the reflector 22' completely protects the areas in which a viewer's eyes, represented by points 38, 39, may be positioned within a very large angular subtence of the visor. FIG. 3b illustrates a set of similar holographic reflectors 26' utilized in a goggle device.

Figure 4A:
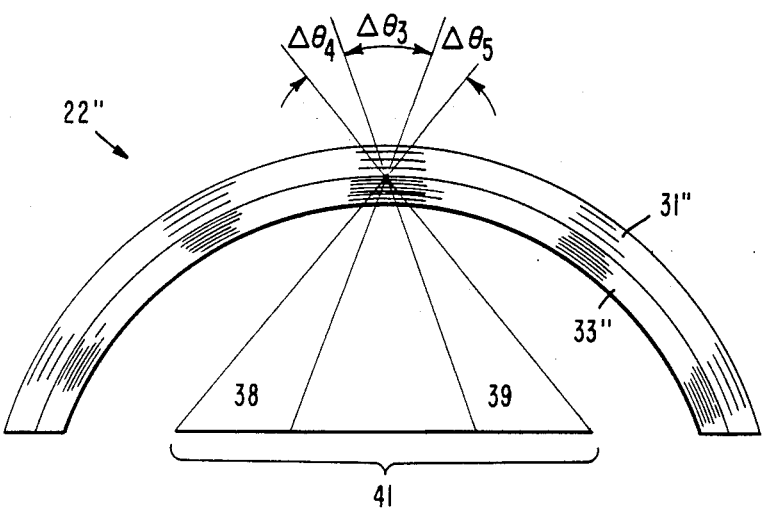
FIGS. 4a and b illustrate embodiments of visor and goggle designs employing a second embodiment of the holographic reflector of the present invention.
Figure 4B:
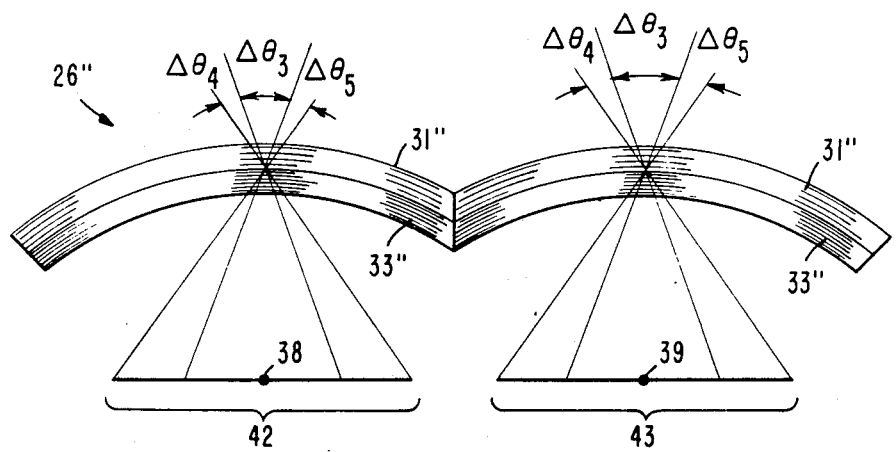

FIG. 4a shows a second embodiment of a holographic visor employing a holographic reflector 22" in accordance with the present invention. This embodiment employs holograms 31", 33" having fringes which are parallel to the substrate surface, but whose relative fringe spacing differs by a predetermined amount. Each of the holograms 31", 33" protect a predetermined angular subtence which is shown as $\Delta\theta_3$ for the first hologram 31" and segments $\Delta\theta_4$ and $\Delta\theta_5$ for the second hologram 33". In this particular device, the first and second holograms 31", 33" are designed so that each hologram reflects a predetermined peak wavelength but the wavelength reflection bandwidths of both holograms 31', 33' overlap, although this is not an absolute requirement. This difference in peak reflection wavelength is accomplished by controlling the fringe spacing and slant angle of each hologram 31", 33". The two holograms 31", 33" protect the entire area of the eyes 38, 39, as shown by bracket 41. FIG. 4b illustrates a second embodiment of a goggle device employing a holographic reflector 26" which utilizes the parallel fringe holograms 31", 33" described with reference to FIG. 4a. Each hologram set protects one of the eyes 38, 39 as shown by brackets 42, 43.

The theory needed for the mechanical construction of the holograms utilized in the above-described embodiments is generally known in the art. There are existing mathematical relationships between peak reflection wavelength, reflection bandwidth, slant angle, fringe spacing, hologram thickness and reflection angles which may be found in references such as a book entitled "Optical Holography" by Collier et al, Academic Press, 1971. This text shows the mechanics of building a hologram to achieve a given peak reflection wavelength, etc., to meet the needs of the present invention.

Figure 5:
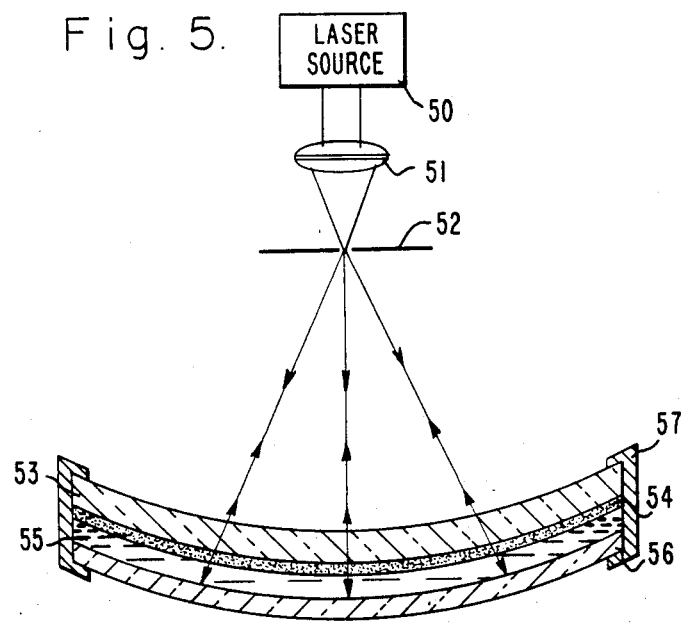
FIG. 5 illustrates one method of making parallel fringe holograms utilized in the present invention.

FIG. 5 illustrates a typical system which may be employed to manufacture the holograms utilized in the parallel fringe devices of the present invention. A laser light source 50 is utilized to provide a point source light image such as may be accomplished by use of a focusing lens 51 and a pinhole aperture 52. The light emitted through the aperture 52 is reflected from a front surface mirror 56. The light rays are transmitted through a substrate 53 which has a holographic recording material 54 disposed on one surface thereof. An index matching fluid 55, such as mineral oil, or the like, is disposed between the holographic material 54 and the mirror 56. The various elements (53-56) are disposed in a support housing 57. The light rays reflect from the mirror 56 back through the fluid 55, the holographic recording material 54 and substrate 53. The interference patterns caused by the counter-propagating light rays form a hologram in the recording material 54. The substrate 53 and the holographic material 54 are removed after the hologram has been recorded and subjected to further processing to finalize the peak wavelength at which the completed hologram reflects light. This processing is generally well-known in art and will not be described herein. The specific manufacturing methods which may be used to construct such holograms are described in numerous sources, including books entitled "Optical Holography" by Collier et al, Academic Press, 1971, and "Holographic Recording Materials" edited by H. M. Smith, Springer Verlay, 1977.

Figure 6:
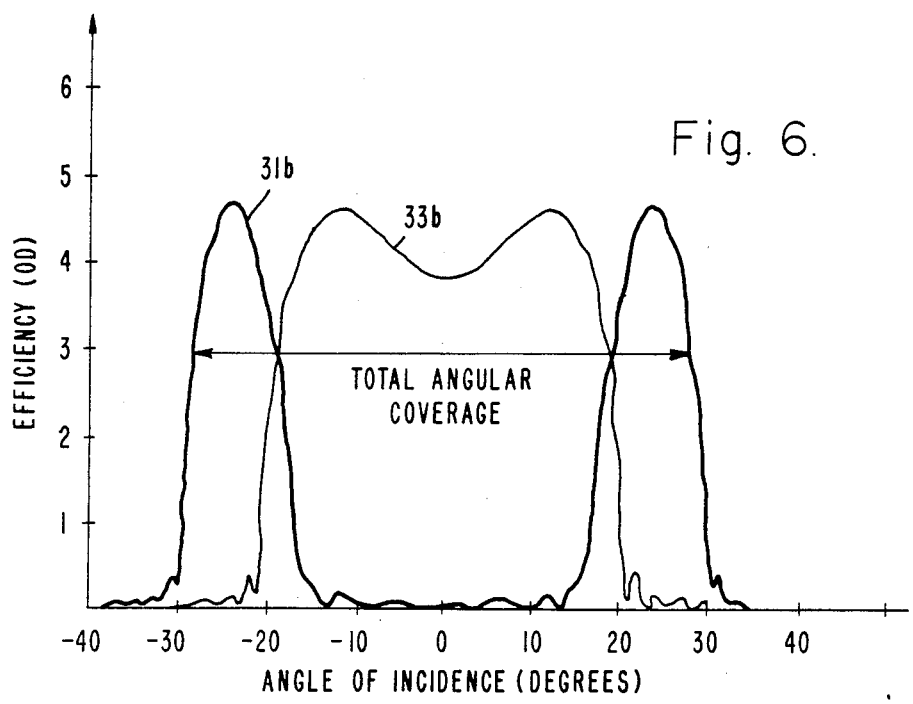
Figure 7:
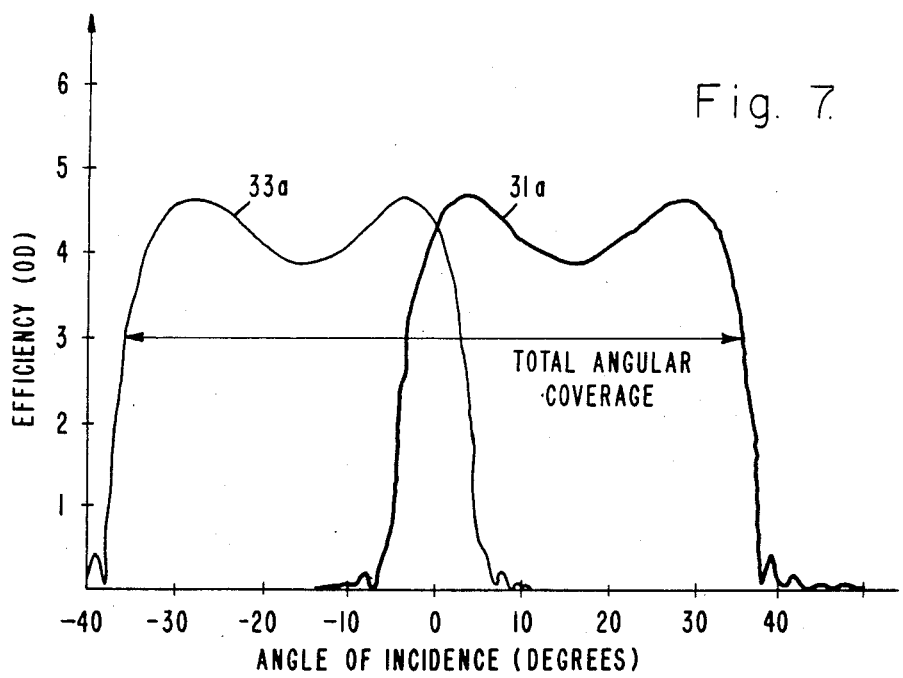

FIGS. 6 and 7 show graphs of reflection efficiency versus angle of incidence for the parallel fringe hologram devices and slanted fringe hologram devices, respectively. The angular coverages of the various holograms 31', 33', 31", 33" shown in FIGS. 6 and 7 correspond to the angular coverages shown in FIGS. 3 and 4, respectively. The angular coverage provided by holograms 31', 33' are shown by graphs 31a, 33a in FIG. 7, while the angular coverage provided by holograms 31", 33" are shown in graphs 31b, 33b of FIG. 6. The horizontal arrows indicate the total angular coverages provided by the respective holgraphic reflectors.

For the purpose of completeness, and as an example of a specific design, a holographic reflector may be designed utilizing either parallel or slanted fringes to provide a minimum of OD 3.0 protection from laser radiation at 0.53 microns. OD, or optical density, is known to those skilled in the holography art, and is defined as the logarithm to the base 10 of the power ratio. Thus, a power ratio of 1000 is OD 3.0. In a parallel fringe device, a visor with a radius of curvature of 4.5 inches may be placed at a distance of 3.5 inches from the eyes. The holographic reflector comprises two holograms, one with a peak wavelength at 0.535 microns covering incident angles from −20° to +20°, and the other at 0.55 microns covering incident angles from −29° to −19° and +19° to +29°. Each hologram should have a peak efficiency of about OD 4.5 in order to provide overall laser radiation rejection of OD 3.0. In a goggle configuration, two holographic reflectors of the same design will be placed at a distance of 1.25 inches from the eyes to provide the same OD 3.0 rejection.

As an example of the slanted fringe device, a fringe slant angle of 10° allows a visor design with a visor-to-eye distance of approximately 2.75 inches for two holograms peaked at 0.535 microns. One hologram covers incident angles from −3° to +36° and the other covers angles from −36° to +3°. In the goggle configuration, the holograms may be placed at a distance of 1.0 inch from the eyes.

As an example of a device which provides reflection at infrared wavelengths, such as might be required by a thermal viewing system, a parallel fringe device providing such protection at 1.06 microns comprises two holograms, one reflecting a peak wavelength at 1.07 microns and the other having a peak wavelength at 1.1 microns. Similarly, a 10° slanted fringe device has two holograms peaked at 1.07 microns.

The above-described embodiments have employed two conterminous adjacent holograms predetermined angular range. It is to be understood that additional pairs of holograms designed for other wavelengths or angular coverages may be stacked adjacently to provide multiple wavelength protection. Thus a plurality of sets of holograms may be employed to provide selective laser wavelength protection. Also, a greater angular coverage may be provided by the use of three or more holograms, if required. These may be adjacently stacked in a manner as shown in FIG. 2a.

Thus, there has been described a new and improved holographic reflector which reflects laser radiation at a predetermined wavelength within a predetermined angular band. The device may employ either parallel fringe or slanted fringe holograms which individually reflect laser radiation within predetermined angular limits. The devices provide excellent laser radiation rejection while allowing clear vision at visible wavelengths.

It is to be understood that the above-described embodiments are merely illustrative of some of the many specific embodiments which represent applications of the principles of the present invention. Clearly, numerous and varied other arrangements may be readily devised by those skilled in the art without departing from the spirit and scope of the invention.

What is claimed is:

1. A holographic reflector for reflecting laser radiation at a predetermined wavelength which is incident over a predetermined angular range, said reflector comprising:

a plurality of holograms conterminously and adjacently disposed on at least one substrate, each of said holograms having holographic fringes with predetermined spacing which make a predetermined angle with respect to the normal to the surface of said substrate, each of said holograms having fringe spacings which are different from the fringe spacing of a hologram adapted to optimally reflect said predetermined wavelength, each of said plurality of holograms having fringe spacings and predetermined angles which are adapted to reflect said predetermined wavelength over separate angular ranges which are different from an angular range associated with a hologram adapted to optimally reflect said predetermined wavelength, said fringe spacings and predetermined angles being such that each of said holograms reflects said predetermined wavelength within said predetermined angular ranges which together comprise said predetermined angular range.

2. The holographic reflector of claim 1 wherein said plurality of holograms comprises two holograms, each of said holograms having holographic fringes which are uniformly slanted with respect to said substrate surface and the fringes of one hologram with respect to the other hologram are oppositely aligned, and the fringe spacings of said two holograms are substantially identical.

3. The holographic reflector of claim 1 wherein said plurality of holograms comprises two holograms, each of said holograms having holographic fringes which are parallel to the surface thereof and the fringe spacing is different for each hologram.

4. The holographic reflector of claim 1 which comprises a plurality of sets of holograms, each set of holograms designed to reflect a separate predetermined wavelength within predetermined angular ranges.

5. A holographic reflector for reflecting laser radiation at a predetermined wavelength which is incident over a predetermined angular range, said reflector comprising a plurality of holograms conterminously and adjacently disposed on at least one substrate, each of said holograms having holographic fringes with predetermined fringe spacing which make a predetermined angle with respect to the normal to the surface of said substrate, wherein said improvement comprises:
each of said holograms having fringe spacings which are different from the fringe spacing of a hologram adapted to optimally reflect said predetermined wavelength, each of said holograms having fringe spacings and predetermined angles which are adapted to reflect said predetermined wavelength over separate angular ranges which are different from an angular range associated with a hologram adapted to optimally reflect said predetermined wavelength, said predetermined fringe spacings and associated predetermined angles being selected such that each of said holograms are optimized to reflect radiation at wavelengths different from said predetermined wavelength along a direction normal to said substrate, said fringe spacings and predetermined angles being such that each of said holograms reflects said predetermined wavelength within predetermined angular ranges which together comprise said predetermined angular range.

6. The holographic reflector of claim 5 wherein said fringes are parallel to the surface of each hologram and the fringe spacing is different for each hologram.

7. The holographic reflector of claim 6 which comprises a plurality of sets of holograms, each set of holograms designed to reflect a separate predetermined wavelength within predetermined angular ranges.

8. The Holographic reflector of claim 5 wherein said fringes are uniformly slanted with respect to the normal to the surface of said substrate and oppositely aligned with respect to each other, and the fringe spacings of said holograms are substantially identical.

9. The holographic reflector of claim 8 which comprises a plurality of sets of holograms, each set of holograms designed to reflect a separate predetermined wavelength within predetermined angular ranges.

10. The holographic reflector of claim 5 which comprises a plurality of sets of holograms, each set of holograms designed to reflect a separate predetermined wavelength within predetermined angular ranges.

11. A holographic reflector for reflecting laser radiation at a predetermined wavelength which is incident over a predetermined angular range, said reflector comprising a plurality of holograms conterminously and adjacently disposed on at least one substrate, each of said holograms having holographic fringes with predetermined fringe spacing which make a predetermined angle with respect to the normal to the surface of said substrate, wherein said improvement comprises:
each of said holograms having fringe spacings which are different from the fringe spacing of a hologram adapted to optimally reflect said predetermined wavelength, said fringes being parallel to the surface of each hologram and the fringe spacing being different for each hologram, said predetermined fringe spacings and associated predetermined angles being such that each of said holograms are adapted to optimally reflect radiation at wavelengths different from said predetermined wavelength, said fringe spacings and predetermined angles being selected such that their associated holograms have predetermined angular coverages at said predetermined wavelength which together comprise said predetermined angular range.

12. A holographic reflector for reflecting laser radiation at a predetermined wavelength which is incident over a predetermined angular range, said reflector comprising a plurality of holograms conterminously and adjacently disposed on at least one substrate, each of said holograms having holographic fringes with predetermined fringe spacing which make a predetermined angle with respect to the normal to the surface of said substrate, wherein said improvement comprises:
each of said holograms having fringe spacings which are different from the fringe spacing of a hologram adapted to optimally reflect said predetermined wavelength, said fringes being uniformly slanted with respect to the normal to the surface of said substrate and oppositely aligned with respect to each other, and the fringe spacings of said holograms being substantially identical, said holograms having predetermined fringe spacings and associated predetermined angles such that each of said two holograms are adapted to optimally reflect radiation at wavelengths different from said predetermined wavelength, said fringe spacings and predetermined angles being selected such that their associated holograms have predetermined angular coverages at said predetermined wavelength which together comprise said predetermined angular range.

* * * * *